(12) United States Patent
Chao et al.

(10) Patent No.: US 9,555,233 B2
(45) Date of Patent: Jan. 31, 2017

(54) ELECTRODE

(71) Applicant: Contour Optik Inc., Chiayi (TW)

(72) Inventors: David Chao, Saratoga, CA (US);
Chien-Ho Lin, Chiayi (TW);
Yung-Chang Chang, Chiayi (TW)

(73) Assignee: Contour Optik Inc., Chiayi (TW)

( * ) Notice: Subject to any disclaimer, the term of this patent is extended or adjusted under 35 U.S.C. 154(b) by 0 days.

(21) Appl. No.: 14/582,567

(22) Filed: Dec. 24, 2014

(65) Prior Publication Data
US 2015/0258329 A1 Sep. 17, 2015

(30) Foreign Application Priority Data
Mar. 14, 2014 (TW) .............................. 103204411 U

(51) Int. Cl.
| | | |
|---|---|---|
| A61N 1/00 | (2006.01) |
| A61N 1/04 | (2006.01) |
| A61N 1/20 | (2006.01) |
| A61N 1/36 | (2006.01) |

(52) U.S. Cl.
CPC ........... *A61N 1/0456* (2013.01); *A61N 1/0472* (2013.01); *A61N 1/20* (2013.01); *A61N 1/0448* (2013.01); *A61N 1/36025* (2013.01)

(58) Field of Classification Search
CPC .. A61N 1/0412; A61N 1/0448; A61N 1/0456; A61N 1/0472; A61N 1/20; A61N 1/0568; A61N 1/36025
See application file for complete search history.

(56) References Cited

U.S. PATENT DOCUMENTS

| | | | |
|---|---|---|---|
| 3,659,614 A | 5/1972 | Jankelson | |
| 7,437,189 B2* | 10/2008 | Matsumura | ............ A61N 1/306 604/21 |
| 2007/0106143 A1* | 5/2007 | Flaherty | ............ A61B 5/04001 600/373 |
| 2010/0204638 A1* | 8/2010 | Hobbs | .................. A61B 18/148 604/20 |
| 2010/0330589 A1* | 12/2010 | Bahrami | ............ A61M 5/1452 435/7.9 |
| 2013/0204315 A1 | 8/2013 | Wongsarnpigoon et al. | |
| 2014/0142676 A1 | 5/2014 | Gardin et al. | |
| 2015/0142078 A1 | 5/2015 | Skaribas | |
| 2015/0217107 A1 | 8/2015 | Walker | |
| 2015/0313496 A1 | 11/2015 | Connor | |

FOREIGN PATENT DOCUMENTS

CN 203075468 U 7/2013

\* cited by examiner

*Primary Examiner* — Mallika D Fairchild
(74) *Attorney, Agent, or Firm* — Fish & Richardson P.C.

(57) ABSTRACT

An electrode configured for use in a direct current electrical stimulation system, which includes a control circuit configured to provide a stimulating current, includes a main body and a plurality of pin members. The main body is electrically coupled to the control circuit to receive the stimulating current therefrom and includes a base wall and a surrounding wall cooperating with the base wall to define a receiving space for receiving an electrically conductive liquid. The pin members extend from the main body, are in fluid communication with the receiving space, and permit delivery of the electrically conductive liquid to a subject when the pin members are placed in direct contact with the subject.

8 Claims, 10 Drawing Sheets

ELECTRODE

CROSS-REFERENCE TO RELATED APPLICATION

This application claims priority of Taiwanese Patent Application No. 103204411, filed on Mar. 14, 2014.

FIELD OF THE INVENTION

The invention relates to an electrode, more particularly to an electrode configured for use in a direct current electrical stimulation system.

BACKGROUND OF THE INVENTION

Conventional acupuncture treatment utilizes various sizes of needles to act on various acupuncture/stimulation points (or acupoints) for stimulating to enhance self healing, blood circulation and metabolism of the patient. However, the conventional acupuncture treatment is invasive and may not be acceptable for some patients.

Another conventional treatment for stimulating the acupuncture points is to utilize moxa, which is to be burnt proximate to the patient's skin at positions corresponding to the acupuncture points, to stimulate the acupuncture points by way of thermal energy (also known as moxibustion). Although such conventional treatment is non-invasive, it may cause burn injuries to the patients (such as blisters) when the burnt moxa is not properly handled.

Recently, scientists have proposed to stimulate the acupuncture points utilizing electrical currents. Chinese patent application publication No. CN203075468U discloses a conventional electrode that can be used in a direct current electrical stimulation system to enhance drug absorbing efficiency. The conventional electrode includes an electrode layer and a hydro-gel adhesive layer disposed to contact directly the patient's skin for enhancing the transmission of a stimulating current to the stimulating points of the patient. However, the hydro-gel adhesive layer may be peeled off from the electrode layer, resulting in poor adhesion of the conventional electrode to the patient's skin.

US patent application publication No. 20130204315 discloses a conventional transcranial direct current electrical stimulation system, which comprises an electrode set including a conventional electrode to provide electrical current stimulation to patients. The conventional electrode includes a sponge portion configured to be secured to the subject/patient's head during the direct current stimulation process, and a stimulating portion inserted or positioned behind the sponge portion. However, such conventional electrode may need to be soaked in conductive liquid manually in advance to perform the direct current electrical stimulation treatment, thereby resulting in some inconvenience.

SUMMARY OF THE INVENTION

Therefore, the object of the present invention is to provide an electrode that may alleviate at least one of the aforementioned drawbacks associated with the prior arts.

According to one aspect of the present invention, an electrode configured for use in a direct current electrical, stimulation system, which includes a control circuit configured to provide a stimulating current, is provided. The electrode includes a base wall and a plurality of electrically-conductive pin members. The base wall is made of an elastically-deformable material and is configured to be electrically coupled to the control circuit to receive the stimulating current therefrom. The pin members extend from and are electrically coupled to the base wall. The pin members are elastically deformable and form a path for transmission of the stimulating current to a subject when the pin members are placed in direct contact with the subject. The electrically conductive material of the base wall is one of an elastically deformable material and a non-elastically deformable material. When the base wall is made of the non-elastically deformable material, the pin members have non-identical lengths.

According to another aspect of the present invention, an electrode configured for use in a direct current electrical stimulation system, which includes a control circuit configured to provide a stimulating current, is provided. The electrode includes a main body and a plurality of elastically-deformable hollow pin members. The main body is made of an electrically conductive material and is configured to be electrically coupled to the control circuit to receive the stimulating current therefrom. The main body includes a base wall and a surrounding wall extending from the base wall and cooperating with the base wall to define a receiving space for receiving an electrically-conductive liquid. The pin members extend from and are electrically coupled to the main body. The elastically-deformable hollow pin members extend from the main body and are in fluid communication with the receiving space. The elastically-deformable hollow pin members permit delivery of the electrically-conductive liquid in the receiving space to a subject when the pin members are placed in direct contact with the subject.

According to yet another aspect of the present invention, an electrode set for a direct current electrical stimulation system, which includes a control circuit configured to provide a stimulating current, is provided. The electrode set includes a plurality of electrodes each independently being one of a dry electrode and a wet electrode.

The dry electrode includes a base wall and a plurality of electrically conductive pin members. The base wall is made of an electrically conductive material and is configured to be electrically coupled to the control circuit to receive the stimulating current therefrom. The electrically conductive pin members extend from and are electrically coupled to the base wall. The pin members are elastically deformable and form a path for transmission of the stimulating current to a subject when the pin members are placed in direct contact with the subject. The electrically conductive material of the base wall is one of an elastically deformable material and a non-elastically deformable material. When the base wall is made of the non-elastically conductive material, the pin members have non-identical lengths.

The wet electrode includes a main body and a plurality of elastically-deformable hollow pin members. The main body is made of an electrically conductive material and is configured to be electrically coupled to the control circuit to receive the stimulating current therefrom. The main body includes a base wall and a surrounding wall extending from the base wall of the main body and cooperating with the base wall of the main body to define a receiving space for receiving an electrically-conductive liquid. The elastically-deformable hollow pin members extend from the main body and are in fluid communication with the receiving space. The hollow pin members permit delivery of the electrically-conductive liquid in the receiving space to the subject when the hollow pin members are placed in direct contact with the subject.

BRIEF DESCRIPTION OF THE DRAWINGS

Other features and advantages of the present invention will become apparent in the following detailed description of the embodiments with reference to the accompanying drawings, of which.

DETAILED DESCRIPTION OF THE EMBODIMENTS

Figure 1:
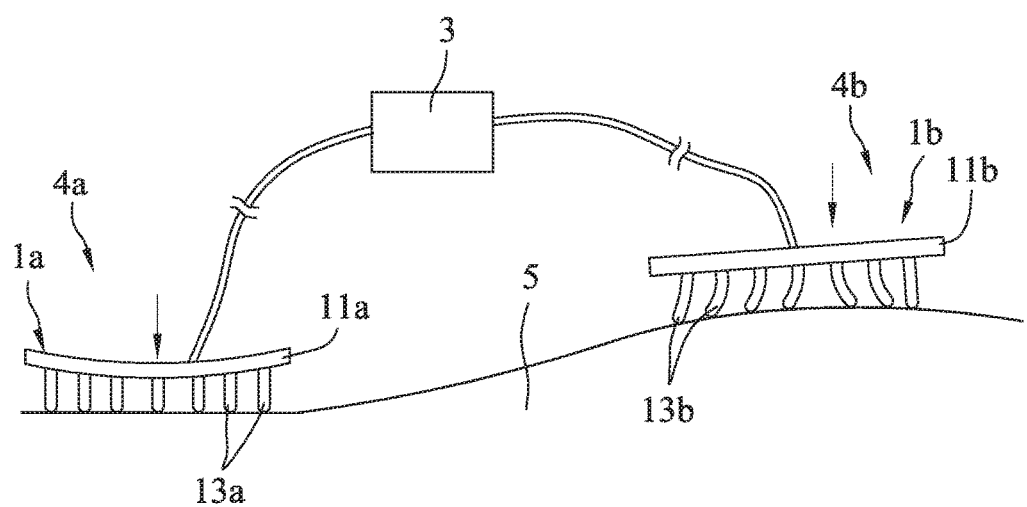
FIG. 1 is a schematic diagram of a first exemplary embodiment of an electrode set including two variations of a dry electrode according to the present invention.

Before the present invention is described in greater detail, it should be noted that like elements are denoted by the same reference numerals throughout the disclosure.

Referring to FIG. 1, the first exemplary embodiment of an electrode set, which is configured for use in a direct current electrical stimulation system (not shown in figure, e.g., a transcranial direct current electrical stimulation system (TDCS)), is shown to include two variations of a dry electrode (i.e., a first electrode 4a and a second electrode 4b as shown in FIG. 1) according to the present invention. The first and second electrodes 4a, 4b are configured to be electrically coupled to a control circuit 3 of the direct current electrical stimulation system which is configured to provide a stimulating current. As shown in FIG. 1, when the first and second electrodes 4a, 4b are in direct contact with various stimulating points of a subject 5 (e.g., a patient), the control circuit 3, the first and second electrodes 4a, 4b and the subject 5 cooperatively form a loop, so that the stimulating current may be transmitted to the subject 5 via the first and second electrodes 4a, 4b. It should be noted that although two electrodes are exemplified in the electrode set of this embodiment, the number of the electrodes used in the electrode set is not limited hereto and may be different (for example, more than two) in other embodiments according to the present invention.

The first electrode 4a includes a base wall 11a and a plurality of electrically conductive pin members 13a. The base wall 11a is made of an electrically-conductive material and is configured to be electrically coupled to the control circuit 3 to receive the stimulating current therefrom. The electrically-conductive material can be selected from the group consisting of a metal material, an electrically-conductive rubber material, an electrically-conductive plastic material, and combinations thereof. The electrically conductive pin members 13a extend from and are electrically coupled to the base wall 11a. In addition, the pin members 13a are elastically deformable and form a path for transmission of the stimulating current to the subject 5 when the pin members 13a are placed in direct contact with the subject 5. In this embodiment, the base wall 11a of the first electrode 4a is elastically deformable, and the pin members 13a have identical lengths. Such configuration of the first electrode 4a allows the pin members 13a to fully contact with the stimulating point or points of the subject 5 when the base wall 11a is pressed to elastically deform, so as to assure effective transmission of the stimulating current from the pin members 13a to the stimulating point or points of the subject 5. In this embodiment, each of the pin members 13a has a distal end that is away from the base wall 11a, and the distal ends of the pin members 13a are arranged on an imaginary curved surface that is substantially concave toward the base wall 11a. However, it should be noted that the configuration of the imaginary curved surface is not limited to what is disclosed in this embodiment, and the imaginary curved surface constituted by the distal ends of the pin members 11a may be configured into other shapes, such as a plane, a convex surface, or curved surfaces corresponding in shape to contact surfaces of the subject 5.

The second electrode 4b, which is similar to the first electrode 4a, includes a base wall 11b and a plurality of pin members 13b. The main difference between the first and second electrodes 4a, 4b resides in that the base wall 11b of the second electrode 4b is not elastically deformable, and that the pin members 13b may have non-identical lengths. However, the distal ends of the pin members 13b are still arranged on an imaginary curved surface that is substantially concave toward the base wall 11b and that corresponds in shape to contact surfaces of the subject 5. Therefore, when the second electrode 4b is placed to be in direct contact with the stimulating point or points of the subject 5 as shown in FIG. 1, the pin members 13b may deform to increase the contact area with the subject 5 so as to fully cover the stimulating point or points of the subject 5 and to assure effective transmission of the stimulating current.

Figure 2:
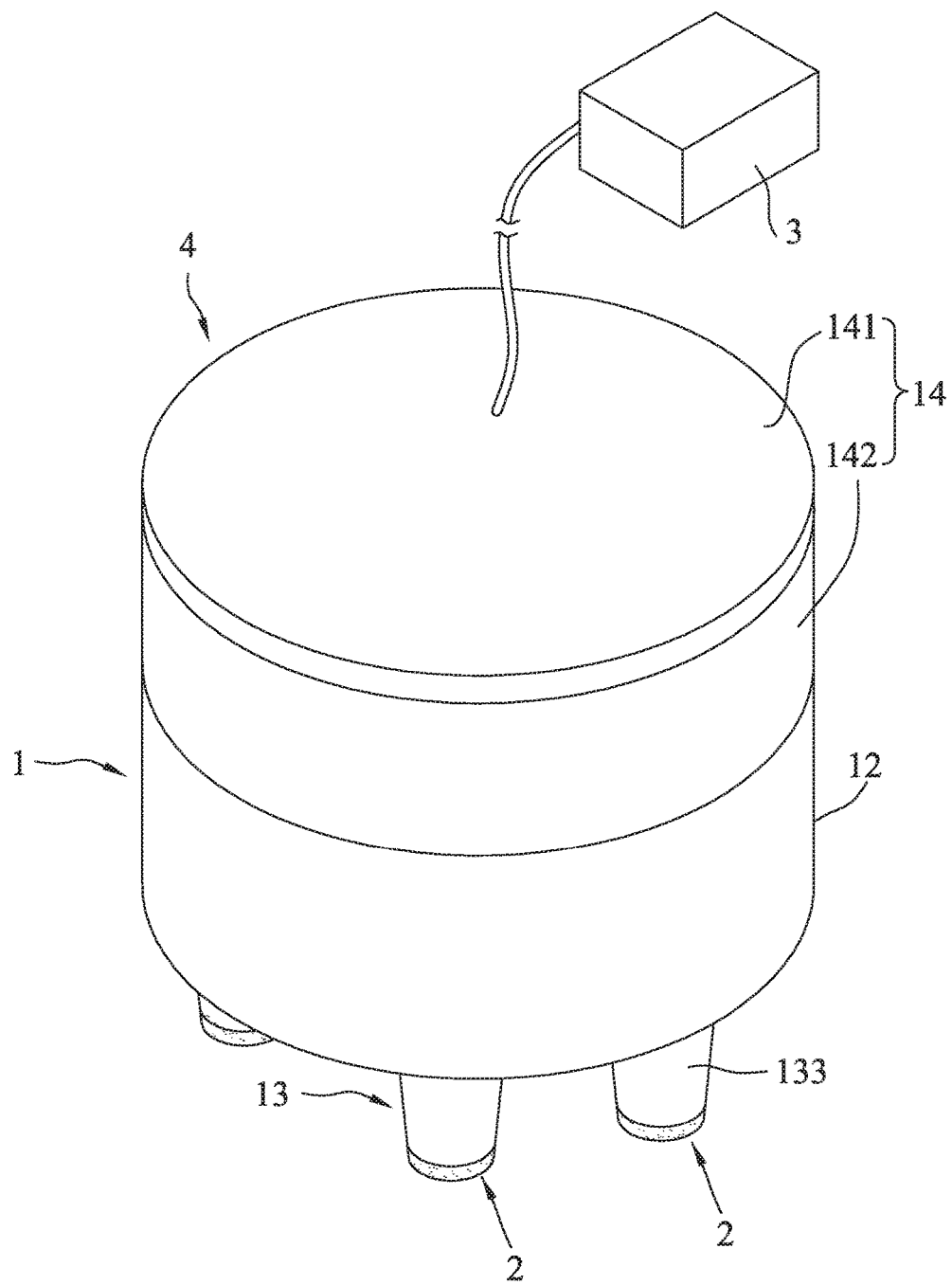
FIG. 2 is a perspective view of a second exemplary embodiment of the electrode according to the present invention.
Figure 3:
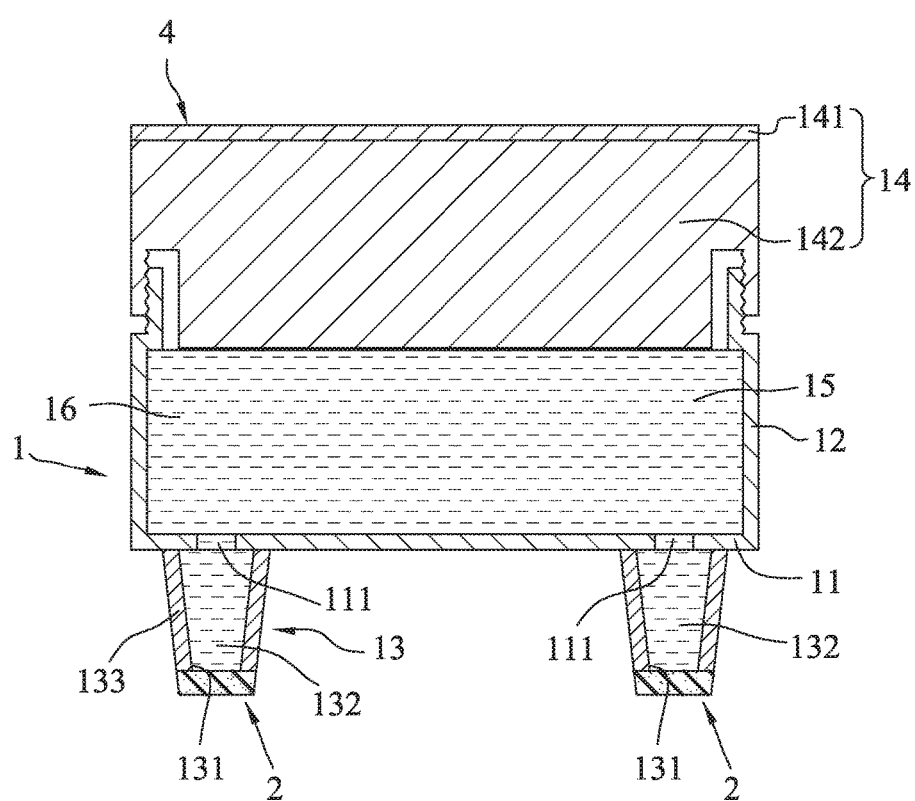
FIG. 3 is a sectional view of the second exemplary embodiment.

Referring to FIGS. 2 and 3, the electrode 4 of the second exemplary embodiment according to the present invention is a wet electrode configured for use in the electrode set of the direct current electrical stimulation system and includes a main body 1 and a plurality of elastically-deformable pin members 13. It should be noted that the electrode set may include at least two electrodes 4 but only one electrode 4 is depicted in the figures. In practice, the electrode 4 may be used with a dry electrode, such as those of the first exemplary embodiment.

As shown in FIGS. 2 and 3, the main body 1 is substantially configured in a post shape and is made of an electrically conductive material, which may be selected from the group consisting of a metal material, an electrically-conductive rubber material, an electrically-conductive plastic material, and combinations thereof. The main body 1 includes a circular base wall 11 and a surrounding wall 12 extending from the base wall 11 and cooperating with the base wall 11 to define a receiving space 16 for receiving an electrically-conductive liquid 15. In this embodiment, the electrically-conductive liquid 15 may be, but is not limited to, saline or an electrically-conductive gel (such as hydro-gel). In this embodiment, the base wall 11 may be elastically deformable and is formed with a plurality of through holes 111 in fluid communication with the receiving space 16. It is worth noting that the main body 1 further includes a driving mechanism 14 that is disposed on the surrounding wall 12 to close one side of the receiving space 16 and that is operable to drive the electrically-conductive liquid 15 in the receiving space 16 to flow toward the base wall 11. In greater detail, the driving mechanism 14 of this embodiment includes an interconnecting component 141 that is electrically coupled to the control circuit 3, and a driving component 142 that is connected to the interconnecting component 141, that is threadedly coupled to the surrounding wall 12 and that is movable toward or away from the base wall 11 to vary a volume of the receiving space 16 via a corresponding one of the through holes 111.

The elastically-deformable hollow pin members 13 extend from the base wall 11 and are in fluid communication with the receiving space 16. The pin members 13 permit the delivery of the electrically conductive liquid 15 in the receiving space 16 to the subject when the pin members 13 are placed in direct contact with the subject. In this embodiment, each of the hollow pin members 13 includes a tubular pin body 133 that is electrically conductive and elastically deformable and that extends from the base wall 11, and a contact body 2 that is elastically deformable and liquid-permeable (such as sponge) and that is disposed at the pin body 133. The tubular pin body 133 of each of the hollow pin members 13 defines a channel 132 that is in fluid communication with the receiving space 16 via a corresponding one of the through holes 111, and the contact body 2 of each of the pin members 13 is configured to permit passage of the electrically-conductive liquid 15 in the channel 132 of a respective one of the pin bodies 133 therethrough. In this embodiment, the pin body 133 of each of the pin members 13 has an opening for exit of the electrically-conductive liquid 15 from the corresponding channel 132, and the contact body 2 of the respective one of the pin members 13 is disposed to cover the opening of the pin body 133. To be specific, the pin body 133 has a distal end 131 that is distal from the base wall 11 and that is formed with the opening.

Figure 4:
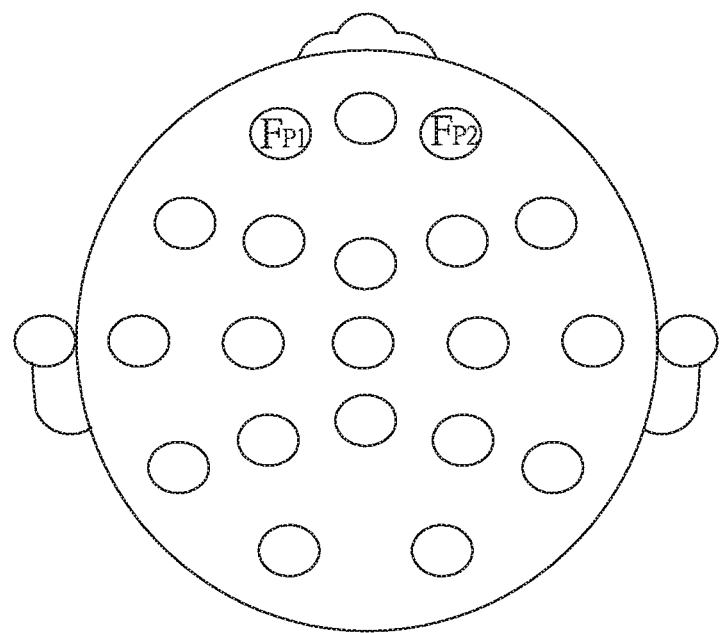
FIG. 4 is a top view of a subject/patient's cranium, illustrating various stimulating points that are suitable for application with the electrode of the present invention.

Further referring to FIG. 4, there are illustrated schematically various stimulating points on a patient's cranium which are suitable for direct current electrical stimulation treatment based on various indications. For example, if the patient wishes to improve his/her memory, stimulating points FP1 and FP2 (see FIG. 4) can be selected and two of the electrodes 4 of the present invention may be attached directly and respectively to these stimulating points to perform the direct current electrical stimulation treatment. It should be noted that the contact bodies 2 of the electrode 4 may non be electrically-conductive at first instance due to the lack of the electrically-conductive liquid (hydro-gel) 15. Thus, before attaching the electrode 4 onto one of the stimulating points of the subject/patient, the subject/patient may utilize the driving mechanism 14 to drive the electrically-conductive liquid 15 in the receiving space 16 to flow into the contact bodies 2 via the through holes 111 and the channels 132, respectively. When the contact bodies 2 are soaked with the electrically-conductive liquid 15 and are in direct contact with the corresponding stimulating points, direct current electrical stimulation treatment may then proceed. In this embodiment, the driving component 142 may be moved toward the base wall 11 by rotating the same relative to the surrounding wall 12, thereby reducing the volume of the receiving space 16 to push the electrically-conductive liquid 15 to flow toward the channels 132 of the pin members 13 via the through holes 111 of the base wall 11. During the direct current electrical stimulation treatment, if the content of the electrically-conductive liquid 15 in the contact bodies 2 is reduced such as due to evaporation and thus lowers the transmission efficiency of the stimulating current to the subject/patient, the driving component 142 may be moved toward the base wall 11 again to push more electrically-conductive liquid 15 out of the channels 132 and into the contact bodies 2, so as to ensure that the content of the electrically-conductive liquid 15 in the contact bodies 2 is sufficient to perform the direct current electrical stimulation treatment.

It is worth noting that, in this embodiment, the contact bodies 2 may be detached from the pin bodies 133 of the electrode 4 for cleaning purposes and may be replaceable to maintain a relatively good condition of the electrode 4 for direct current electrical stimulation treatment.

Figure 5:
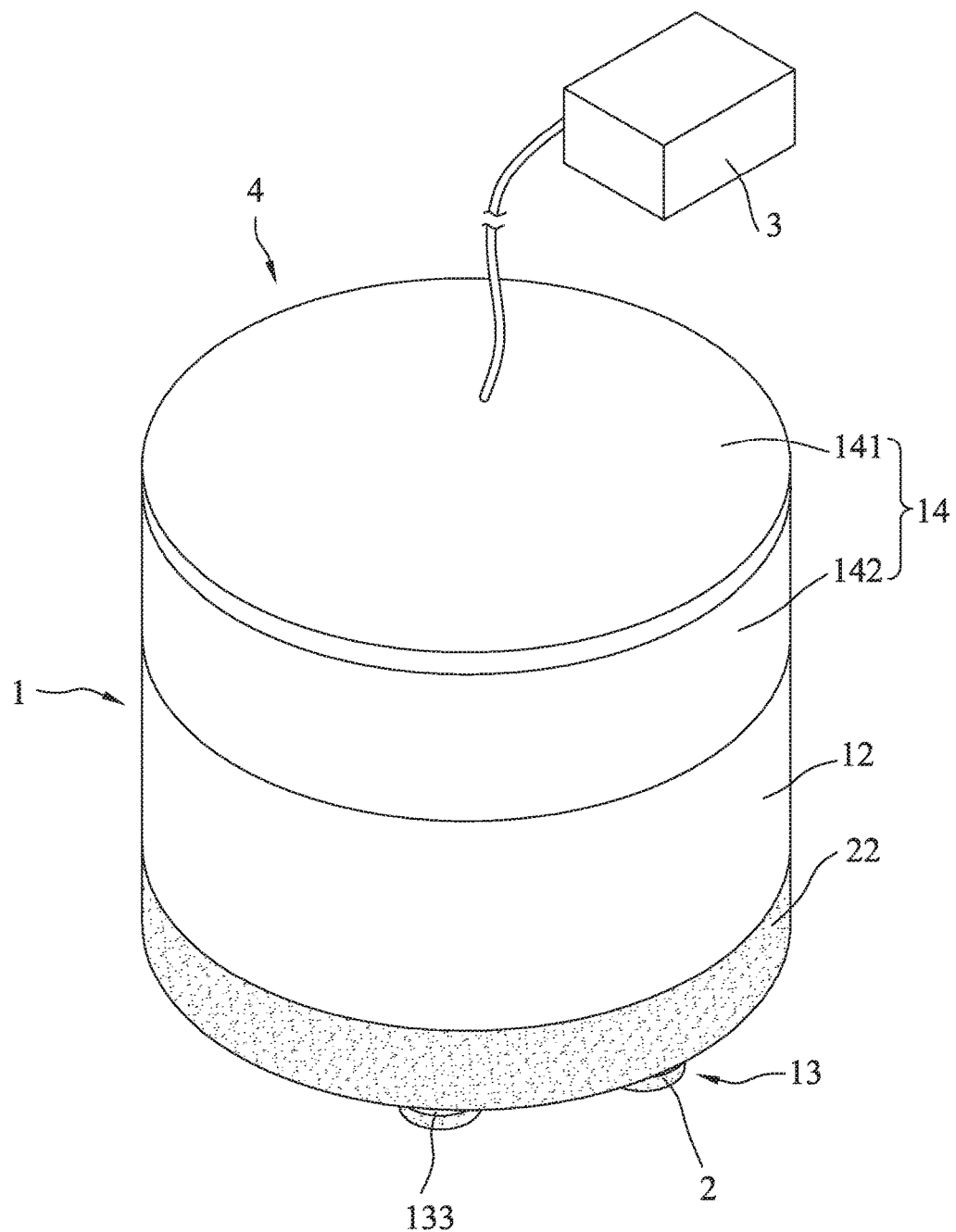
FIG. 5 is a perspective view of a third exemplary embodiment according to the present invention.
Figure 6:
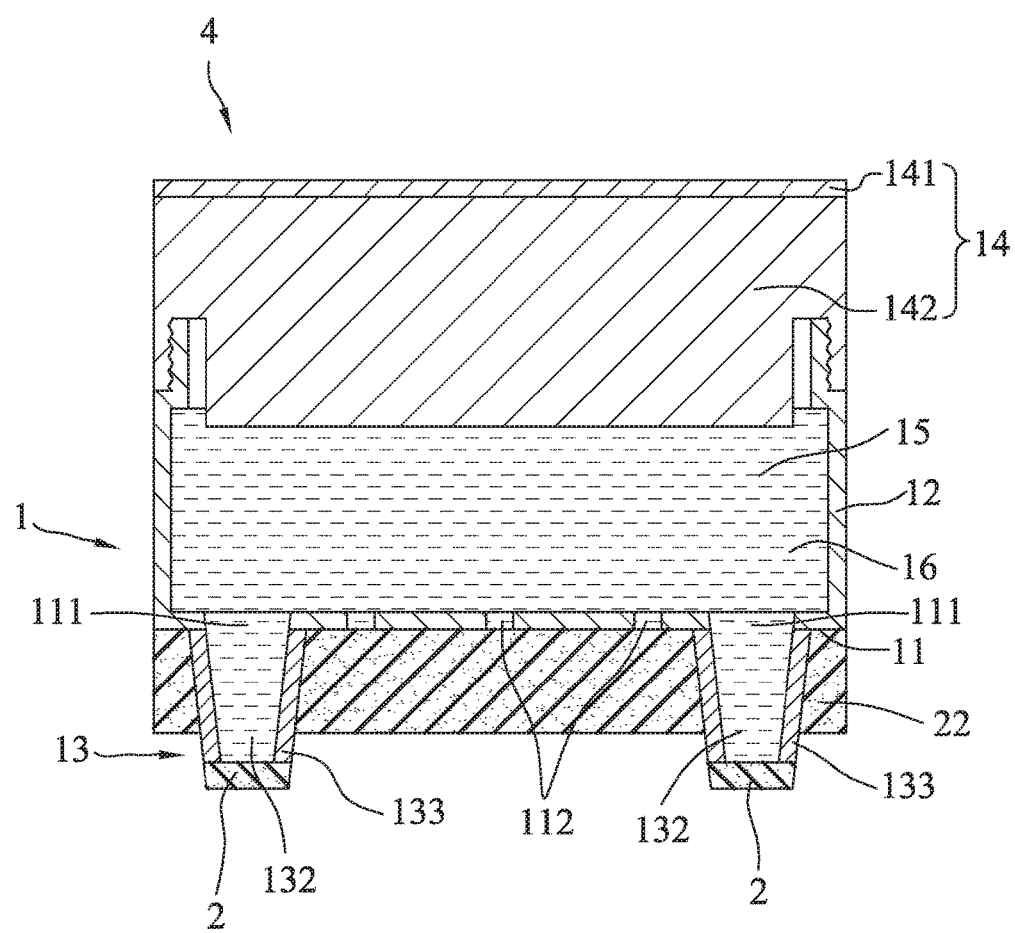
FIG. 6 is a sectional view of the third exemplary embodiment.

Referring to FIGS. 5 and 6, the third exemplary embodiment of the electrode 4 according to the present invention is shown to be similar to that of the second exemplary embodiment. The differences therebetween reside in that the base wall 11 of the third exemplary embodiment is further formed with at least one auxiliary through hole 112 in fluid communication with the receiving space 15 and offset from the pin members 13, and that the electrode 4 further comprises a liquid-permeable layer 22 abutting against one side of the base wall 11 opposite to the receiving space 15 and disposed to cover the at least one auxiliary through hole 112. Such configuration of this embodiment allows the electrically-conductive liquid 15 to flow into the liquid-permeable layer 22, which may provide the same to the subject/patient when in direct contact therewith, so that frequent operation of the driving mechanism 14 may not be required. In this embodiment, the liquid-permeable layer 22 is made of a material the same as that of the contact bodies 2.

Figure 7:
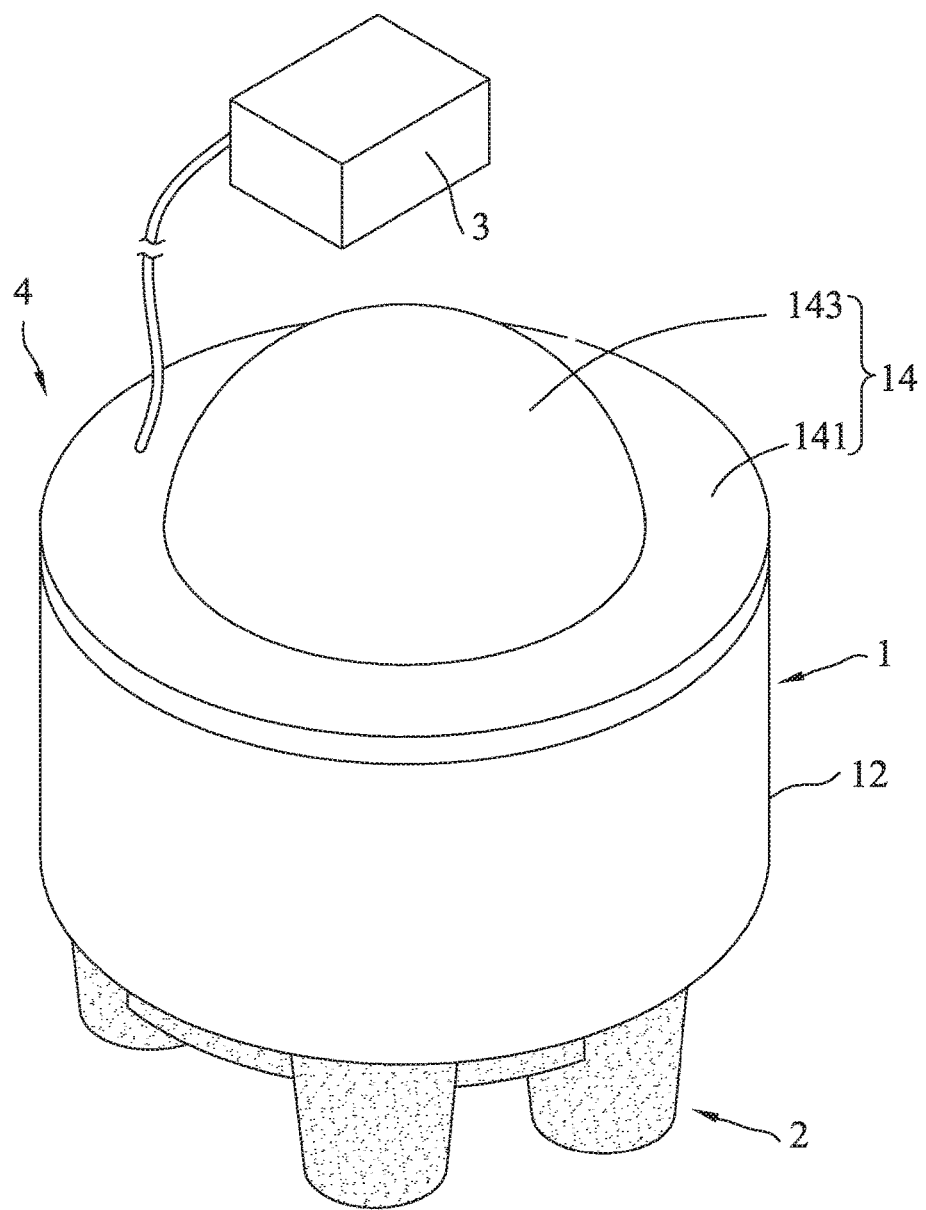
FIG. 7 is a perspective view of a fourth exemplary embodiment of the electrode according to the present invention.
Figure 8:
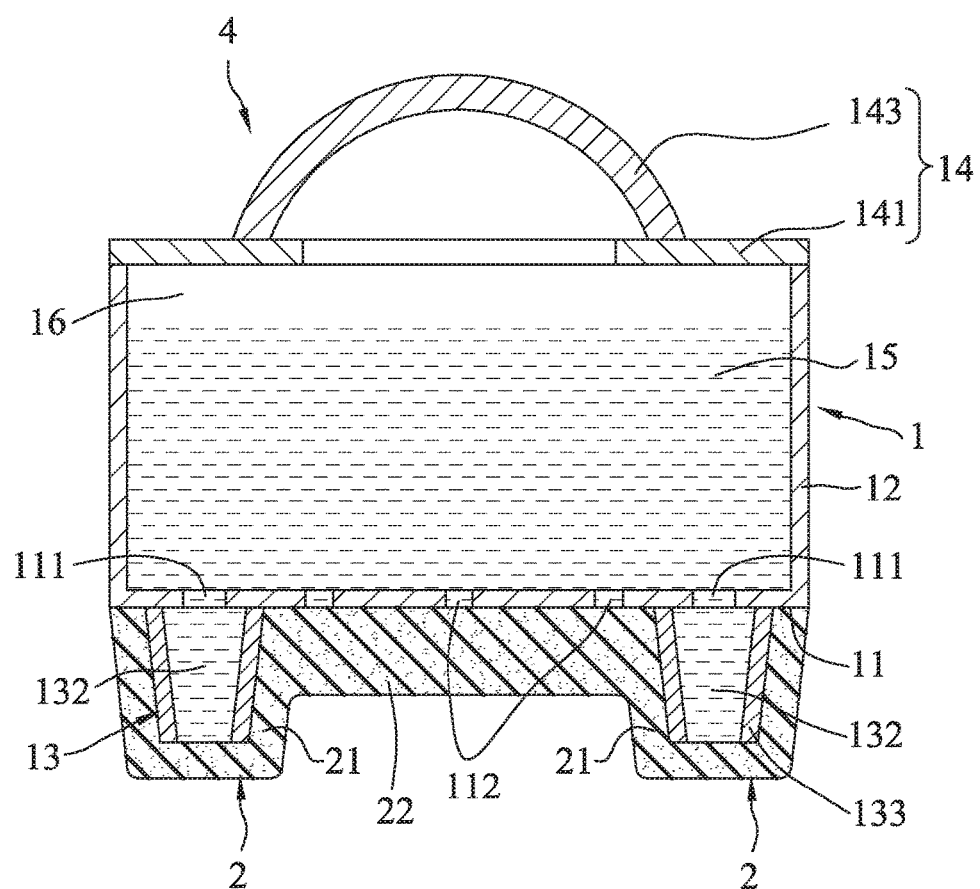
FIG. 8 is a sectional view of the fourth exemplary embodiment.

Referring to FIGS. 7 and 8, the fourth exemplary embodiment of the electrode 4 according to the present invention is shown to be similar to that of the third exemplary embodiment. The differences therebetween reside in the following. Each of the contact bodies 2 of the fourth exemplary embodiment further has an extension part 21 that surrounds the distal end of a respective one of the pin bodies 133 and that is connected to the liquid-permeable layer 22. In addition, the driving mechanism 14 includes a driving component 143 that is connected to the interconnecting component 141, and that is formed with a button portion which is deformable upon pressing, so as to force the electrically-conductive liquid 15 in the receiving space 16 to flow toward the base wall 11. The driving mechanism 14 may be formed with an air vent (not shown). The fourth exemplary embodiment has the advantages as those of the third exemplary embodiment.

Figure 9:
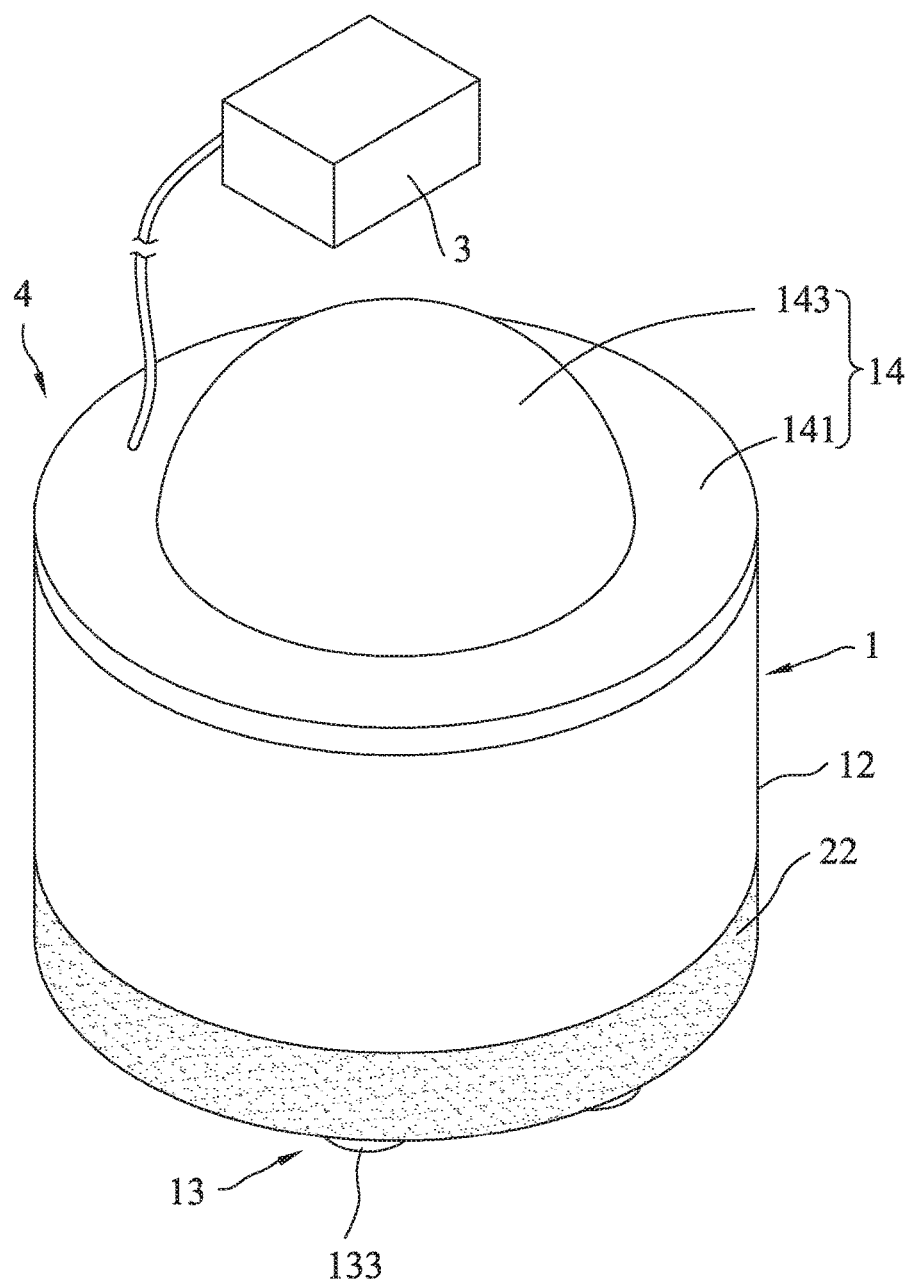
FIG. 9 is a perspective view of a fifth exemplary embodiment according to the present invention.
Figure 10:
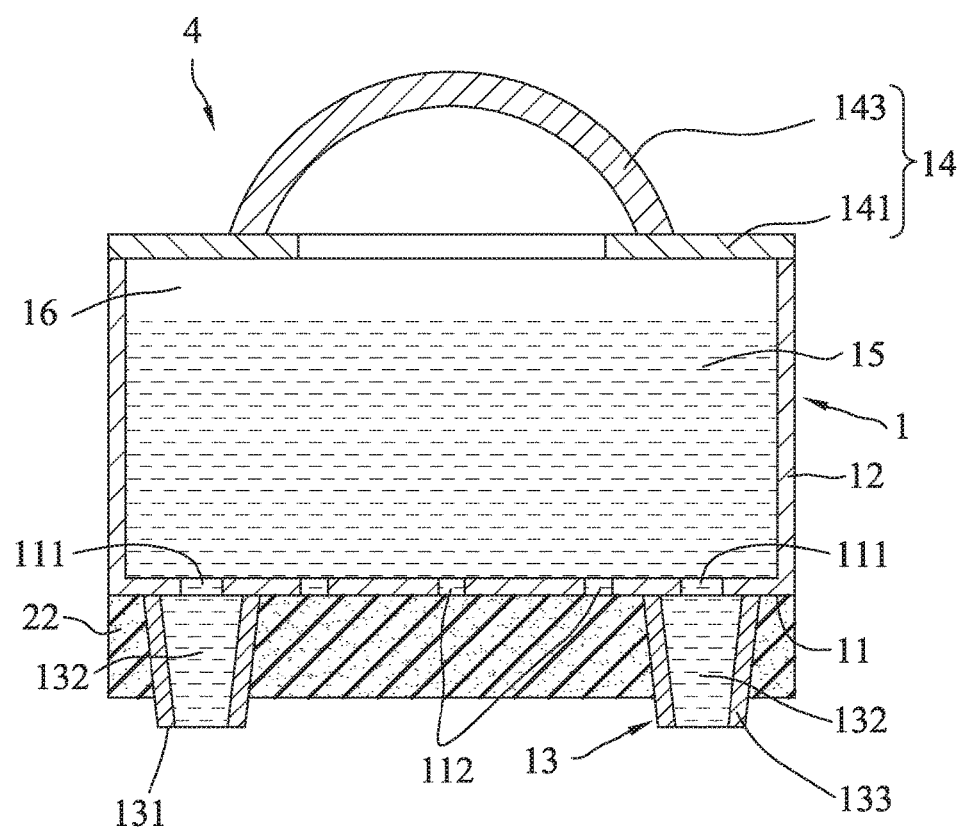
FIG. 10 is a sectional view of the fifth exemplary embodiment.

Referring to FIGS. 9 and 10, the fifth exemplary embodiment of the electrode 4 according to the present invention is shown to be similar to that of the third embodiment. The difference therebetween resides in that the contact bodies 2 are omitted in this embodiment, and that the driving mechanism 14 of the fifth exemplary embodiment includes the driving component 143 which is similar to that of the fourth exemplary embodiment. The fifth exemplary embodiment has the advantages similar to those of the third exemplary embodiment.

It is worth mentioning that the electrode set used in the direct current electrical stimulation system can include the electrodes 4 of various embodiments according to the present invention.

To sum up, each of the elastically-deformable pin members 13 of the electrode 4 according to the present invention can be placed in full contact with the subject/patient by way of deformation. Moreover, the base wall 11 of the electrode 4 may be elastically deformable as well to further increase the contact area of the pin members 13 with the subject/patient. Furthermore, the electrically-conductive liquid 15 can be stored in the receiving space 16 of the main body 1 and delivered to the contact bodies 2 via the through holes 111 and the channels 132 based on demand, so as to ensure the effective transmission of the stimulating current to the subject/patient. Even further, the contact bodies 2 of the electrode 4 can be detached from the pin bodies 133 for cleaning purposes and may be replaceable.

While the present invention has been described in connection with what are considered the most practical embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An electrode configured for use in a direct current electrical stimulation system, which includes a control circuit configured to provide a stimulating current, said electrode comprising:
   a main body that is made of an electrically conductive material, that is configured to be electrically coupled to the control circuit to receive the stimulating current therefrom, and that includes a base wall and a surrounding wall extending from said base wall and cooperating with said base wall to define a receiving space for receiving an electrically-conductive liquid; and
   a plurality of elastically-deformable hollow pin members that extend from said main body and that are in fluid communication with said receiving space, said pin members permitting delivery of the electrically-conductive liquid in said receiving space to a subject when said pin members are adapted to be placed in direct contact with the subject;
   wherein each of said pin members includes: an elastically-deformable electrically-conductive tubular pin body extending from said base wall, electrically coupled to said main body, and defining a channel that is in fluid communication with said receiving space; and an elastically-deformable liquid-permeable contact body disposed at said pin body and configured to permit passage of the electrically-conductive liquid in said channel therethrough;
   wherein said base wall of said main body is formed with a plurality of through holes in fluid communication with said receiving space, said channel of each of said pin members being in fluid communication with said receiving space via a corresponding one of said through holes; and
   wherein said base wall is further formed with at least one auxiliary through hole in fluid communication with said receiving space and offset from said pin members, said electrode further comprising a liquid-permeable layer abutting against one side of said base wall opposite to said receiving space and disposed to cover said at least one auxiliary through hole.

2. The electrode according to claim 1, wherein said pin body has an opening for exit of the electrically-conductive liquid from said channel, and said contact body is disposed to cover said opening of said pin body.

3. The electrode according to claim 2, wherein said pin body has a distal end that is distal from said base wall and that is formed with said opening.

4. The electrode according to claim 1, wherein:
   said pin body has a distal end that is distal from said base wall, that extends through said liquid-permeable layer, and that has an opening for exit of the electrically-conductive liquid from said channel; and
   said contact body is disposed to cover said opening of said pin body.

5. The electrode according to claim 4, wherein said contact body has an extension part that surrounds said distal end of said pin body and that is connected to said liquid-permeable layer.

6. The electrode according to claim 1, wherein the electrically-conductive material is selected from the group consisting of a metal material, an electrically-conductive rubber material, an electrically-conductive plastic material, and combinations thereof.

7. An electrode configured for use in a direct current electrical stimulation system, which includes a control circuit configured to provide a stimulating current, said electrode comprising:
   a main body that is made of an electrically conductive material, that is configured to be electrically coupled to the control circuit to receive the stimulating current therefrom, and that includes a base wall and a surrounding wall extending from said base wall and cooperating with said base wall to define a receiving space for receiving an electrically-conductive liquid; and
   a plurality of elastically-deformable hollow pin members that extend from said main body and that are in fluid communication with said receiving space, said pin members permitting delivery of the electrically-conductive liquid in said receiving space to a subject when said pin members are adapted to be placed in direct contact with the subject;
   wherein said main body further includes a driving mechanism that is disposed on said surrounding wall and that is operable to drive the electrically-conductive liquid in said receiving space to flow toward said base wall; and
   wherein said driving mechanism includes a driving component that is threadedly coupled to said surrounding wall and that is movable toward or away from said base wall to vary a volume of said receiving space.

8. An electrode configured for use in a direct current electrical stimulation system, which includes a control circuit configured to provide a stimulating current, said electrode comprising:
   a main body that is made of an electrically conductive material, that is configured to be electrically coupled to the control circuit to receive the stimulating current therefrom, and that includes a base wall and a surrounding wall extending from said base wall and cooperating with said base wall to define a receiving space for receiving an electrically-conductive liquid; and
   a plurality of elastically-deformable hollow pin members that extend from said main body and that are in fluid communication with said receiving space, said pin members permitting delivery of the electrically-conductive liquid in said receiving space to a subject when said pin members are adapted to be placed in direct contact with the subject;
   wherein said main body further includes a driving mechanism that is disposed on said surrounding wall and that is operable to drive the electrically-conductive liquid in said receiving space to flow toward said base wall; and
   wherein said driving mechanism includes a driving component that is formed with a button portion which is deformable upon pressing so as to force the electrically-conductive liquid to flow toward said base wall.

* * * * *